United States Patent [19]

Avery et al.

[11] Patent Number: 5,725,493
[45] Date of Patent: Mar. 10, 1998

[54] INTRAVITREAL MEDICINE DELIVERY

[76] Inventors: Robert Logan Avery, 659-C Del Parque Dr., Santa Barbara, Calif. 93103; Jeffrey Kevin Luttrull, 3160 Telegraph Rd. Suite 230, Ventura, Calif. 93003

[21] Appl. No.: 353,804

[22] Filed: Dec. 12, 1994

[51] Int. Cl.$^6$ .................. A61M 5/00; A61M 35/00
[52] U.S. Cl. ............................. 604/9; 604/294
[58] Field of Search ............ 604/8, 9, 10, 294; 424/427

[56] References Cited

U.S. PATENT DOCUMENTS

| | | | |
|---|---|---|---|
| 3,916,899 | 11/1975 | Theeuwes et al. | 120/260 |
| 4,543,088 | 9/1985 | Bootman et al. | 604/93 |
| 4,553,973 | 11/1985 | Edgren | 424/427 |
| 4,751,926 | 6/1988 | Sasaki | 128/303 R |
| 4,781,675 | 11/1988 | White | 604/10 |
| 5,171,213 | 12/1992 | Price, Jr. | 604/9 |
| 5,178,604 | 1/1993 | Baerveldt et al. | 604/8 |

OTHER PUBLICATIONS

Michelson, et al; Experimental Endophthalmitis Treated With an Implantable Osmotic Minipump; Arch Opthalmol–vol. 97, Jul. 1979; pp. 1345–1346.

Eliason et al; An Ocular Perfusion System; Invest. Opthalmol. Vis. Sci., Vol. 19, No. 1, Jan. 1980; pp. 102–105.

Miki et al; A Method For Chronic Drug Infusion Into the Eye; Japanese Jornal of Ophthalmology, vol. 28: 140–146, 1984.

Jabs; Treatment of Cytomegalovirus Retinitis–1992; Arch Ophthlmol–vol. 110, Feb. 1992; pp. 185–187.

Smith et al; Intravitreal Sustained–Release Ganiclovir; Arch Ophthlmol–vol. 110,Feb. 1992; pp. 255–258.

Sanborn et al: Sustained–Release Ganciclovir Therapy for Treatment of Cytomegalovirus Retinitis; Arch Ophthmol–Vol. 110, Feb. 1992; pp. 188–195.

Krupin; Krupin Eye Valve; Hood Laboratories Catalogue F 079 Rev Nov. 1992 Four Pages Unnumbered.

*Optimed*; The Optimed Advantage Glaucoma Pressure Regulator; Optimed Advertising Brochure, Seven Pages Unnumbered; Jour. Glaucoma, vol. 2 #3, 1993.

Kimura et al; A New Vitreal Drug Delivery System Using An Implantable Biodegradable Polymeric Device: Investigative Opthalmology & Visual Science, May, 1994, vol. 35, No. 6; pp. 2815–2819.

Rubsamen et al; Prevention of Experimental Proliferative Vitreoretin–Opathy With a Biodegradable Intravitreal Implant for the Sustained Release of Fluorouracil; Arch Ophthalmol/ vol. 112, Mar. 1994; pp. 407–413.

Hashizoe et al; Scleral Plug of Biodegradable Polymers for Controlled Release in the Vitreous: Arch Ophthalmol/ vol. 112, Oct. 1994; pp. 1380–1384.

*Primary Examiner*—John G. Weiss
*Assistant Examiner*—Dennis Ruhl
*Attorney, Agent, or Firm*—Leo F. Costello

[57] ABSTRACT

An intravitreal medicine delivery device and method that includes an implant device through which a wide variety of beneficial medicines including drugs or other pharmacological agents can be introduced into the vitreous cavity over an extended period of time with only a single initial surgery to implant the device. The device and method minimize the surgical incision needed for implantation and avoid future or repeated invasive surgery or procedures. Additional amounts of the initial medicine can readily be introduced or the medication can be varied or changed, as required. Furthermore, the device and method allow the dosage delivered to the vitreous cavity to be controlled, and the device is constructed so as to filter medicines delivered to the cavity and also avoids damage to or interference with other parts of the eye during implantation or during use.

28 Claims, 5 Drawing Sheets

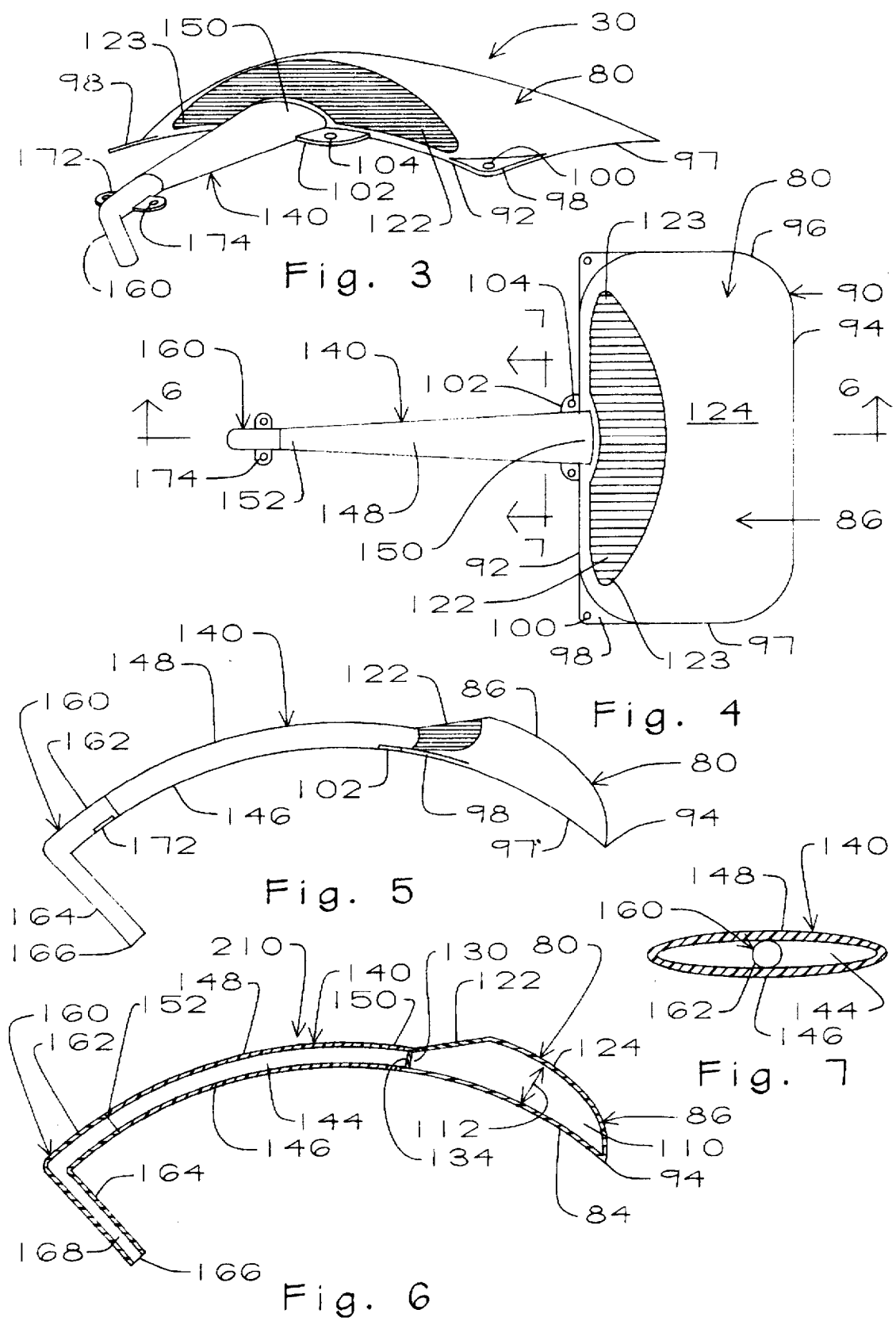

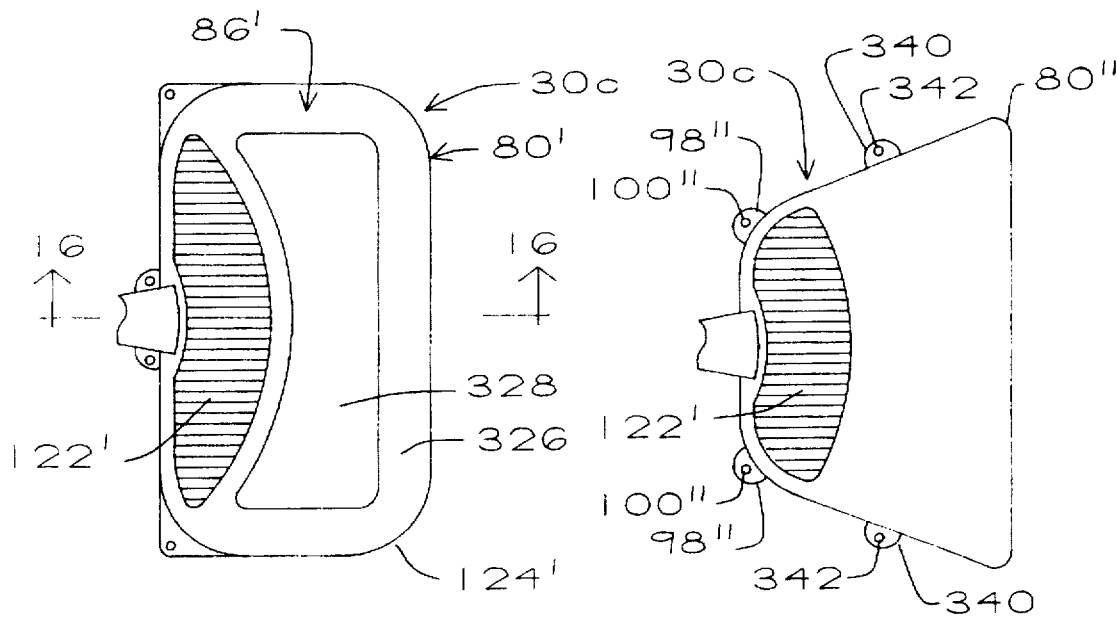
Fig. 14
Fig. 17
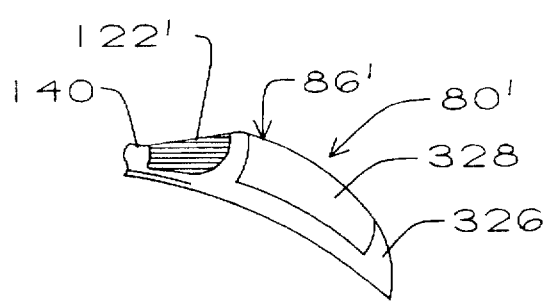
Fig. 15
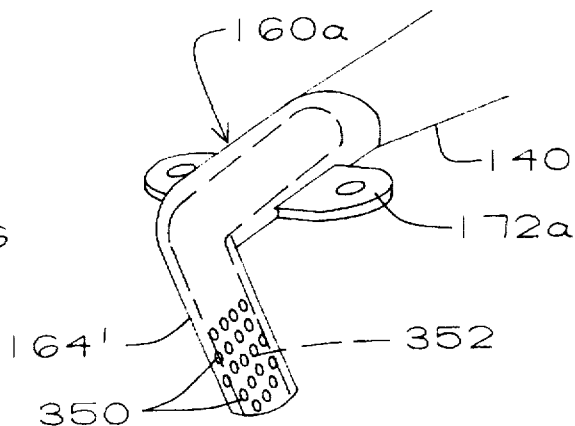
Fig. 18
Fig. 16
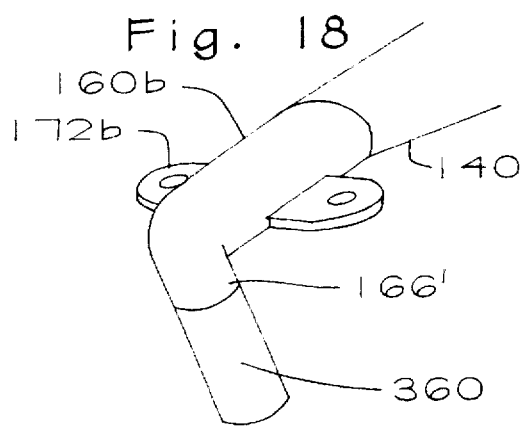
Fig. 19

INTRAVITREAL MEDICINE DELIVERY

FIELD OF THE INVENTION

This invention pertains to intravitreal medicine delivery and more particularly to an implant device for delivering medicine to the vitreal cavity of the eye, and to a method for introducing medicines into the vitreal cavity using the device.

BACKGROUND

Within the past several decades, great advances have been made in the diagnosis and treatment of vitreoretinal diseases. Advances in laser technology, and vitreoretinal surgical techniques, have significantly improved the prognosis of numerous retinal conditions including diabetic retinopathy, macular degeneration, and retinal detachment. As the pathophysiology of these and many other vitreoretinal diseases is also becoming more clearly understood, a host of potential pharmacological agents is currently under investigation.

In addition to the numerous antibiotic, antiviral, and antifungal agents currently used to treat infections of the retina and vitreous, many antiinflammatory and anticancer drugs have been shown to be useful in treating diseases such as proliferative vitreoretinopathy. As the role of growth factors involved in diabetic retinopathy, macular degeneration, and other retinal degenerations is elucidated, new classes of agents have been found to be of possible benefit, including growth factors themselves, blocking antibodies to growth factors, antisense oligonucleotides, and even gene therapy with growth factor inserts.

Unfortunately, the delivery of drugs to the retina is often problematic. Most agents given topically to the eye (in the form of eye drops) do not penetrate through the anterior segment of the eye well enough to reach the vitreous or retina in therapeutic concentrations. Medications can be given orally or intravenously, but the blood vessels within the retina (and other parts of the central nervous system) are relatively impermeable to many agents. Furthermore, these drugs may have significant systemic side effects on other organs of the body. Drugs can be directly injected into the vitreous cavity, via a needle passed through the pars plana, and this technique is currently employed to combat certain severe, sight-threatening infections. However, this procedure itself entails certain risks, such as infection, bleeding, cataract formation, and retinal detachment. Furthermore, the majority of the injected drug is often cleared from the vitreous cavity within several days, necessitating multiple injections for prolonged treatment.

Accordingly, devices have been developed for improving the introduction of drugs to the vitreal cavity. One such device is a biodegradable polymer designed to be injected into the vitreous cavity where it slowly releases drug as it dissolves. A similar drug-containing polymer has been developed which is made in the shape of a tack or plug to be surgically inserted into the eyewall at the pars plana so that it projects into the vitreous cavity. Liposomes containing pharmacological agents have been developed to slowly release the agent after injection into the vitreous cavity. Another device is a plastic pellet which contains a retinal drug (ganoclovir) and is sutured inside of the vitreous cavity where the drug slowly dissolves into the cavity.

Although such devices as those briefly referred to above are apparently effective in delivering drugs into the vitreous cavity, they have significant disadvantages. First, all of these devices contain a certain amount of drug which when expended cannot be replenished without repeating the surgical implantation or intravitreal injection. Although these different devices can release drugs for weeks to months (or in the case of the plastic pellet, almost one year), certain indications for intravitreal drug administration require extended or lifetime therapy. Therefore, multiple procedures are often required and are highly undesirable.

Secondly, the device with the longest release rate, the plastic pellet of ganiclovir, requires a very large eyewall incision (5 mm) to implant due to its large size. Although the other devices can be implanted or injected through a smaller incision (1 mm or less), those that are injected freely into the vitreous cavity instead of anchored to the eyewall can migrate within the eye and come in direct contact with the retina where they can block vision or release high local concentrations of drug which could potentially prove toxic to delicate retinal tissue.

Third, many pharmacological agents cannot easily and effectively be incorporated into biodegradable polymers. Furthermore, many potential pharmacological agents would not remain stable for extended periods of time in the vitreous cavity. Therefore, there is a significant limitation to what pharmacological agents can be administered via the slow release devices currently available.

Fourth, since the plug or pellet is in essence the drug itself, treatment is limited to this drug, so that another surgery or procedure is required to change it if administration of a different drug is desired.

SUMMARY

The present invention is directed to intravitreal medicine delivery involving an implant device and method wherein a wide variety of beneficial drugs or other pharmacological agents or medicines can be introduced into the vitreous cavity over an extended period of time, as much as the life of the patient, with only a single initial surgery to implant the device; wherein the surgical incision needed for implantation is minimized; wherein additional amounts of drugs over an initial supply can be introduced without further invasive surgery; wherein the type of medicine can be varied or changed depending on such factors as the disease being treated or drug availability; wherein the dosage of agent being administered is controllable; and wherein damage or interference by the implant to various parts of the eye is avoided.

It is an object of the present invention to provide for improved delivery of drugs and other pharmacological agents to the vitreous cavity of the eye, especially for treating vitreoretinal diseases.

It is another object to enable medicinal agents to be delivered to the vitreous cavity with a single initial surgery and without the need for repeated invasive surgeries or procedures.

It is yet another object of this invention to allow replenishment of the drug or other medicinal agent within an implant attached to the eyewall by injection into the implant through the conjunctivae and not through the eye wall.

It is further object to be able to change the pharmacological agent being dispensed from an eye implant device into the vitreal cavity, without surgery or other invasive procedure.

It is also an object to control the dosage of drugs or other pharmacological agents delivered to the vitreous cavity from an implant device.

It is still another object of the present invention to enable the patient to control delivery of dosages of medicines to the vitreous cavity with a delivery device implanted on the patient's eyeball.

It is a still farther object to implant an intravitreal medicine delivery device which dispenses medicine into the vitreous cavity without interference with or damage to various parts of the eye.

It is yet another object of the present invention to prevent inadvertent puncture of the eyeball by an injection needle used to replenish the supply of drugs or other agents in an eye implant device.

It is also an object of the subject invention to prevent an uncontrolled movement of medicines into the vitreous cavity from an intravitreal delivery implant when the supply of medicines in the implant is being replenished in situ.

It is another object of this invention to filter medicines being dispensed from an implant device before being admitted to the vitreous cavity thereby to prevent unwanted particulate matter, such as undissolved biodegradable polymer, from moving into the cavity, while allowing medicines to pass into the cavity.

It is a feature of the present invention to have a relatively large drug or other medicine-containing reservoir which is located outside the eyewall in the sub-conjunctival space and which is connected to the vitreous cavity by a smaller tube through the pars plana so that a substantial amount of medicine can be brought into the vitreous cavity with a minimum of eyewall incision.

It is a feature of this invention to provide an intravitreal medicine delivery device with a pump for moving predetermined doses of drugs or other agents into the vitreous cavity and which can be operated by the patient.

It is another feature to provide an intravitreal drug delivery device which has a low profile for closely-fitting implantation under the conjunctiva and Tenon's capsule of the eyeball.

It is another feature of this invention to provide an eye implant device with an injection port which can be readily identified through overlying tissue for injecting an additional supply of medicine into the implant device.

It is still another feature of this invention to suture a medication delivery implant device to the eyewall so that it facilitates subsequent injections of medication into it while maintaining its implanted position.

These and other objects, features, and advantages of the subject invention will become apparent upon reference to the accompanying drawings, the following description, and the appended claims.

DESCRIPTION OF THE DRAWINGS

FIG. 3 is an isometric view of the subject intravitreal medicine delivery device, even further enlarged from the size in FIG. 1 and showing the three principle parts of the device, namely, a housing, a tube, and an elbow.

FIG. 4 is a plan view of the intravitreal medicine delivery device shown in FIG. 3.

FIG. 5 is a side elevation of the device shown in FIG. 4.

FIG. 6 is a cross-section along line 6—6 of FIG. 4.

FIG. 7 is a cross-section along line 7—7 of FIG. 4.

FIG. 14 is a plan view of a portion of the subject medicine delivery device, but depicting another embodiment of the housing of the device.

FIG. 15 is a side elevation of the embodiment of FIG. 14.

FIG. 16 is a cross-section along line 16—16 of FIG. 14.

FIG. 17 is a plan view of a portion of the subject delivery device but depicting still another embodiment of the housing.

FIG. 18 is an isometric view of another embodiment of an elbow of the subject delivery device which differs from the elbow shown in FIG. 3.

FIG. 19 is also an isometric view of still another embodiment of the elbow.

DETAILED DESCRIPTION

Intravitreal Medicine Delivery Device-First Embodiment

Figure 1:
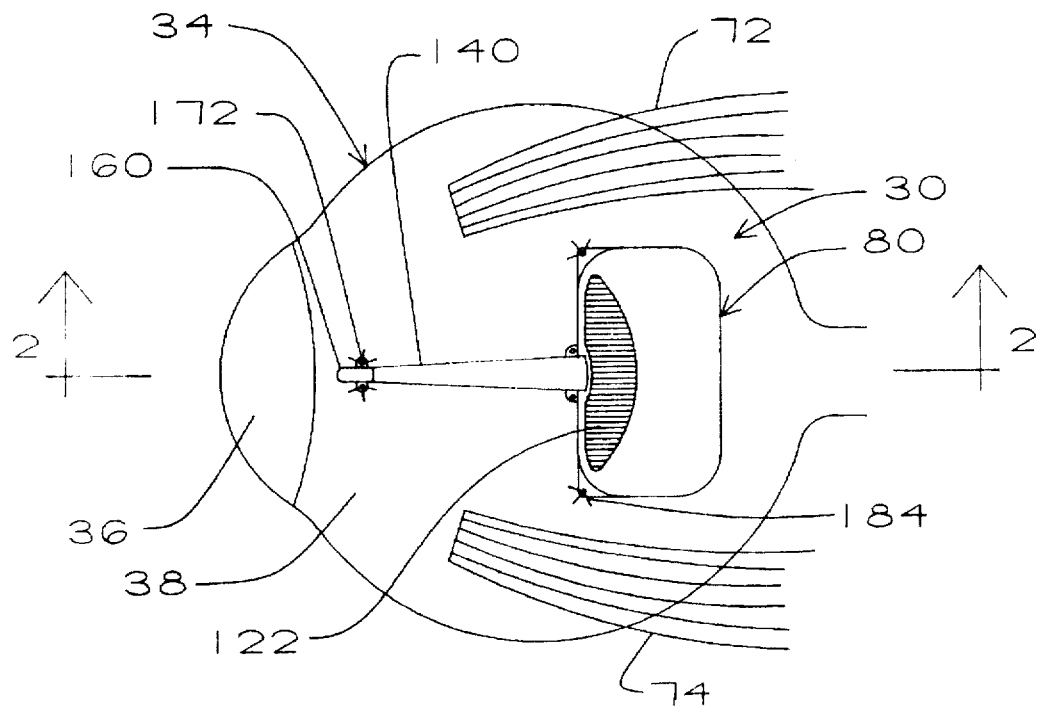
FIG. 1 is a plan view of one embodiment of an intravitreal medicine delivery device according to the present invention shown implanted on a human eyeball, which is schematically shown, it being understood that both the device and the eyeball are enlarged from actual size.
Figure 2:
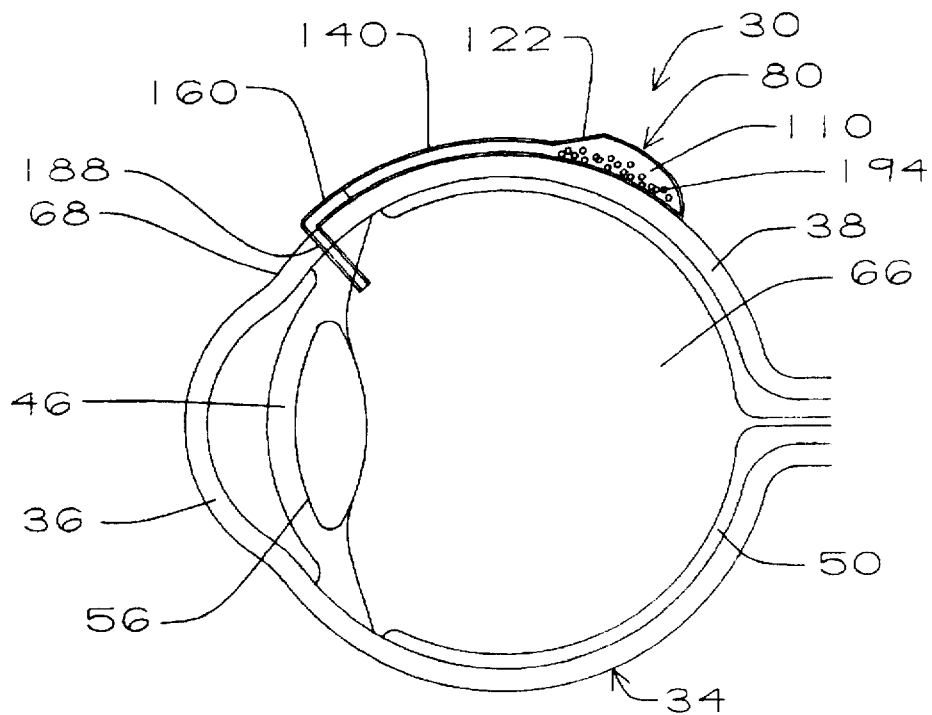
FIG. 2 is a cross-section taken along line 2—2 of FIG. 1.
Figure 8:
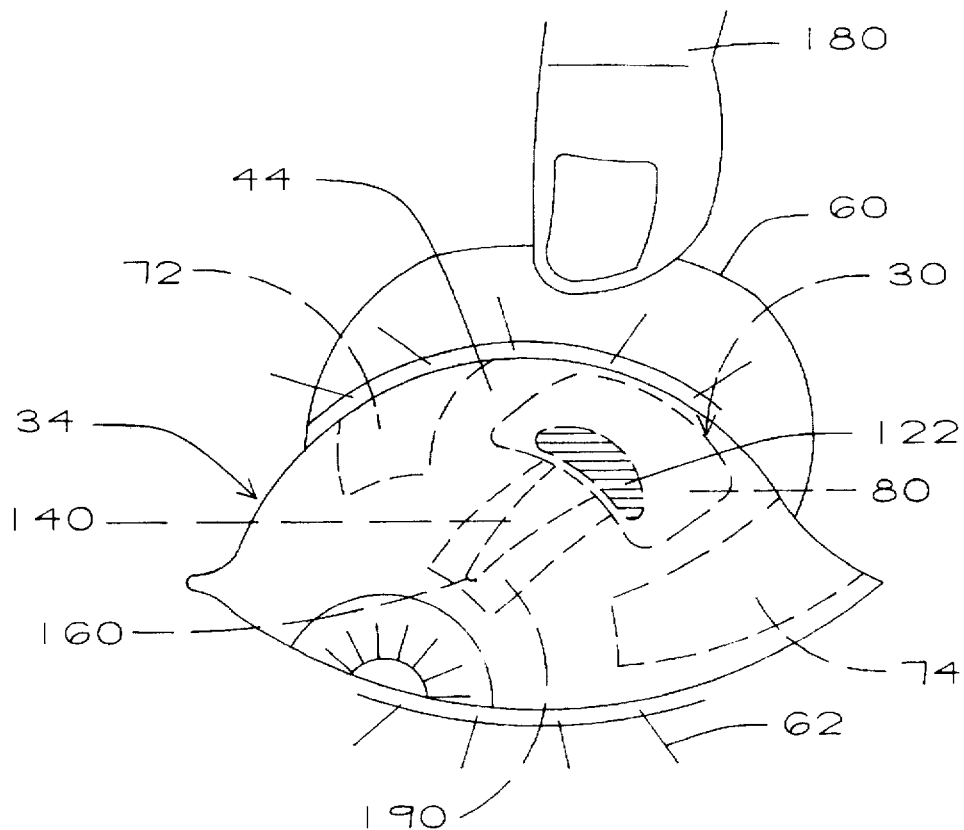
FIG. 8 is a greatly enlarged schematic view of an eye showing the subject intravitreal medicine delivery device implanted on the eyeball and representing the eyelid being lifted to expose the region of the eye where the implant is located.

The first embodiment of an intravitreal medicine delivery device of the present invention is identified in FIGS. 1–6 by the numeral 30 and is shown in FIGS. 1 and 2 as being implanted on a human eyeball or globe 34. The eyeball is shown schematically and in just enough detail to enable an understanding of the present invention. Certain parts of the eye are thus briefly identified with reference numerals. Schematically represented in either or both of FIGS. 1, 2, 8 and 9 are the cornea 36, the sclera 38, the conjunctiva and Tenon's capsule 44, the iris 46, the retina 50, the lens 56, the eyelid 60, eyelashes 62, the vitreous cavity 66, the pars plana 68, the superior rectus muscle 72, and the lateral rectus muscle 74.

The first embodiment of the intravitreal delivery device 30 is shown in detail in FIGS. 3–7 and is now described. The device includes a housing 80 most of which is preferably pre-formed of semi-rigid material to have a concavo-convex shape and a low profile so as during surgery to fit easily and closely against an eyeball, as 34. In plan view the housing preferably has a generally rectangular outline (FIG. 4) or a trapezoidal outline (FIG. 17) but this outline may be varied to facilitate implantation as will be understood by those skilled in the art.

The housing 80 (FIGS. 3–6) has a base or bottom wall 84 which has an outwardly, spherically concave shape or curvature generally complementary to the curvature of the eyeball 34. This bottom wall is made of a tough material impenetrable by an injection needle or syringe and is preferably of a plastic, such as nylon, Kevlar, or polymethyl methacrylate (PMMA), but may be made of metal, such as tantalum. The housing also has a top or upper wall 86 which has an outwardly spherically convex shape and is joined in a fluid-tight manner to the bottom wall along a peripheral edge 90. The top and bottom walls may be one-piece and integral along the edge or of two different pieces sealed along the edge. This edge has an anterior segment 92, a posterior segment 94, and lateral segments 96 and 97 which meet at four corners of the housing. Outer corner fixation tabs 98 project from the anterior corners of the housing and have suture-receiving eyelets 100. Spaced, inner anterior fixation tabs 102 project from the anterior segment 92 and also have suture-receiving eyelets 104.

The spaced top and bottom walls 86 and 84 (FIGS. 5 and 6) provide a fluid-tight storage reservoir or chamber 110 in the housing 80. This reservoir has a maximum height dimension indicated by the numeral 112 and measured radially of the curved top and bottom walls and where the spacing between the walls is the greatest. As an example but not limiting to the invention, this maximum height dimension is preferably about 3–4 mm. Of course, the height of the reservoir tapers downward toward all four segments 92, 94, 96 and 97 (FIGS. 3, 5 and 6) of the edge 90. It is also noted that the lateral dimensions of the reservoir, that is the length and width dimensions, measured generally spherically of the walls, are relatively much greater than the maximum height. For the embodiment shown in FIG. 4, but again not limiting to the invention, the width or distance between lateral edges 96 and 97 is approximately 1.5 cm and the length or distance between the anterior and posterior edges 92 and 94 is approximately 1 cm.

Of particular significance, however, is that the top wall 86 (FIGS. 3–6) of the housing 80 has a slightly uplifted, arcuate, anterior medicine-injection port or area 122 closely adjacent to the anterior edge 92 and having opposite ends 123 closely adjacent to the anterior corners of the housing. The top wall also has a main or remainder portion 124 of greater area than the injection port. This main portion is of the same material as the bottom wall 84 and is the part of the top wall which is joined to the bottom wall. Thus, this main portion is needle-impenetrable and fluid-impervious.

The injection port 122 (FIGS. 3–6), however, is of a material, such as silicone rubber, which is penetrable by a needle or syringe but which reseats itself when the needle is withdrawn so that the port is normally fluid-impervious. An important feature of the port is that the material thereof is colored, for example, blue, as indicated in the drawings. This coloration is important to provide a marker or identification mark which is visible exteriorly of the eye, especially through covering tissue or patches, to facilitate location of the port by attending medical personnel.

The reservoir 110 (FIGS. 5 and 6) has an anterior fluid outlet 130 located in the top wall 86 of the housing 80 between the anterior segment 92 and the injection port 122 and is thus between the inner tabs 102. A filter 134 is optionally mounted in the outlet to prevent particulate materials, such as biodegradable polymer, from passing out of the reservoir and into the vitreous cavity, while permitting medicines released from the dissolving polymers to pass out of the reservoir 110 and into the cavity. This filter may take various forms such as a semi-permeable, osmotic membrane or a porous cellulose filter such as a Millipore filter. Furthermore, it may be a thin capillary tube, or coil of capillary tube, designed to restrict the flow of drug-containing fluid from the reservoir 110 into the vitreous cavity 66.

The subject intravitreal medicine delivery device 30 also includes a tapered, elongated delivery tube 140 (FIGS. 3–7) of fluid-impervious compressible elastomeric material, such as a silicone elastomer, thus providing a fluid passageway or lumen 144. Preferably, the tube is of oval cross-section as illustrated, but is not limited to this cross-section. The tube has a low or flat profile, like the housing, and includes a base and upper walls 146 and 148 which are joined at lateral edges. The passageway has a relatively small minor axis or dimension, as best seen in FIG. 7, which is preferably less than the height maximum height dimension 112 of the reservoir 110. Again, although not limiting to the invention, this minor axis is preferably about the size of a 19–20 gauge lumen. The base wall may be outwardly convex, as shown, or concave to conform to the curvature of the eyeball. Significantly, the top wall is resiliently compressible toward the base wall by applying slight digital pressure against the wall to constrict the passageway. When the pressure is relieved, the top wall returns to its normally relaxed position with the passageway fully open.

The tube 140 (FIGS. 3–7) has a relatively wide proximate end 150 connected to the housing 80 around the outlet 130 so that the passageway 144 is in fluid communication with the reservoir 110. In effect, the passageway is an extension of the reservoir so that the reservoir and the passageway together constitute one large storage reservoir or chamber. The tube converges anteriorly from the housing to a relatively narrow distal end 152, it being noted that the major axis of the passageway thus varies from a maximum at the proximate end to a minimum at the distal end. As shown in FIGS. 5 and 6, the tube is preferably preformed with, and has sufficient rigidity to maintain, a longitudinal curvature complementary to the curvature of an eyeball, but is sufficiently flexible to allow limited flexing at the juncture of the tube and the housing.

The subject delivery device 30 (FIGS. 3–6) also includes a semi-rigid tubular elbow 160 having an in-line connector sleeve 162 attached to the distal end 152 of the tube 140 and an intravitreal extension 164 which projects from the sleeve at an angle to the in-line sleeve, preferably of about eighty to ninety degrees, and terminates in a tip 166. The sleeve is of about the same diameter as the minor axis or height of the tube, as best seen in FIG. 7, and although given by way of example only, is about 19–20 gauge. The elbow thus provides a lumen or fluid passageway 168 in fluid communication with the passageway in the tube and opening at the tip. Another pair of fixation tabs 172 project laterally from the sleeve 162 of the elbow 160 and have suture eyelets 174. The elbow may be made of the same material as the housing.

Once again, to provide an example of a preferred embodiment of the intravitreal delivery device 30 (FIG. 4) but not limiting to the invention, the length of the combined tube 140 and elbow 160, from the anterior segment 92 to the bend of the elbow, is about 7 mm, and the maximum transverse dimension of the tube at its proximate end is about 3 mm.

Intravitreal Medicine Delivery Method

The method of the present invention and use of the subject delivery device 30 are best described by reference to FIGS. 1, 2, 8 and 9. The delivery device is implanted within the socket of the eye on the episcleral surface of the globe (eye wall) 66 by placing the device under the conjunctiva 44 and Tenon's capsule. The device is located between the superior and lateral rectus muscles 72 and 74 with the base wall 84 fitted against the eyeball 34 and the anterior edge 92 located posteriorly of the muscle roots and slightly posteriorly of the equator of the eyeball, as best seen in FIG. 1. Thusly located, the injection port 122 faces anteriorly, and the tube 140 projects anteriorly with the tip 166 at the pars plana 68.

A hole 188 (FIG. 2) of about 1.0 mm is incised through the eyeball 34 at the pars plana 68 and into the vitreous cavity 66. The intravitreal extension 164 of the elbow 160 is inserted through the hole so that it projects into the cavity a distance of preferably approximately 4 mm. In this regard, it is to be noted that the rigidity of the elbow allows the position of the intravitreal extension 164 to be controlled as it is inserted into the cavity so as to avoid contact of the tube with the lens 56, cornea 36 or iris 46. The device 30 is then attached to the episclera 38 with sutures 184 (FIG. 1) in selected eyelets 100 (and/or 104) and eyelets 174 (FIG. 4). The tabs 98 and 102 are provided as alternates in case one location or the other is preferred for the sutures. After suturing the device in place, a sceral patch or graft 190 (FIG. 8) is sutured over the tube 140 for the purpose of preventing of erosion of the implant tube through the conjunctiva, which could lead to infection and require removal of the implant. The rigidity of the elbow and its attachment to the sclera (FIGS. 1 and 2) maintain the intravitreal extension of the implant tube in the position in which it is initially placed so that it does not move around in the cavity as the implant is worn and used by the patient.

A supply of medicine 194 (FIG. 2) is placed in the reservoir 110 before or after implantation. Examples of drugs that may be used are antivirals, antibiotics, steroids, growth factors or inhibitors, anti-sense oligonucleotides, mediators of gene therapy, and others. These may be in the form of fluids, solids, suspensions, emulsions, slow-release or time-release beads, capsules, liposomes, ion-exchange beads, biodegradable polymers, pellets, or other microparticulate vehicles. As an example, the medicine 194 is shown as time-release beads in FIG. 2.

If drugs or other agents are injected after the implant surgery, the eyelid 60 remains lifted (FIG. 8) to expose the region where the device 30 is implanted. Because of its color, the injection port 122 is visible through the conjunctiva tissue 44 covering the device. The tube 140 may be depressed to block the passageway 144 (FIG. 6), and an injection needle 202 of a syringe 200 (FIG. 9) filled with the medicine 194 penetrates the port, and the medicine is injected.

If a large volume of medicine 194 is to be instilled into the reservoir 110 (FIG. 9), either initially or to refill the implant 30 at a later date, venting of the implant reservoir by a second needle, not shown but placed through the injection port 122 simultaneously with injection, may be required. Injection of small volumes of medicine into the reservoir, however, may not require venting.

After the injection is completed (FIG. 9), the needle 202 is withdrawn and the tube 140 is released to expand to normal size (FIG. 2). By blocking the passageway during filling of the reservoir, fluid flow or fluid pressure through the tube and elbow 160 and into the vitreous cavity 66 is precluded. When the needle is withdrawn, the port 122 reseats itself.

Following the implant surgery and as the patient wears the implanted device 30 (FIG. 2), the medicine 194 is thus exposed to the vitreous cavity 66 over an extended period of time. Whether the medicine is in the form of solid material from which the medicine diffuses or whether the medicine is fluid-borne, this exposure through the passageways 144 and 168, allows the medicine to diffuse, flow or otherwise move or pass from the reservoir 110 into the vitreal cavity.

The impetus for diffusion of the medicine 194 from the reservoir 110 into the vitreous cavity 66 occurs for several reasons. First, the concentration gradient between the medicine in the reservoir and vitreous fluid will set up its own diffusion gradient causing a movement of medicine into the cavity. Secondly, the patient can cause flank fluid flow by digitally pressing against the eyelid 60 and thereby against the top wall 148 of the tube 140 to force fluid-borne medicine into the vitreous cavity. Thus, the compressible top wall 148 in combination with the storage reservoir and passageways 144 and 168 may serve as a pump which is generally identified by numeral 210. Thirdly, injection of medicine via reservoir increases pressure in the reservoir driving a net flux of fluid through the tube into the vitreous cavity. Finally, normal physiologic forces, such as blinking, eye movements, and normal blood pressure pulses, will cause small pressure gradients to develop in the implant tube promoting passage of medicine into the vitreous cavity.

Figure 9:
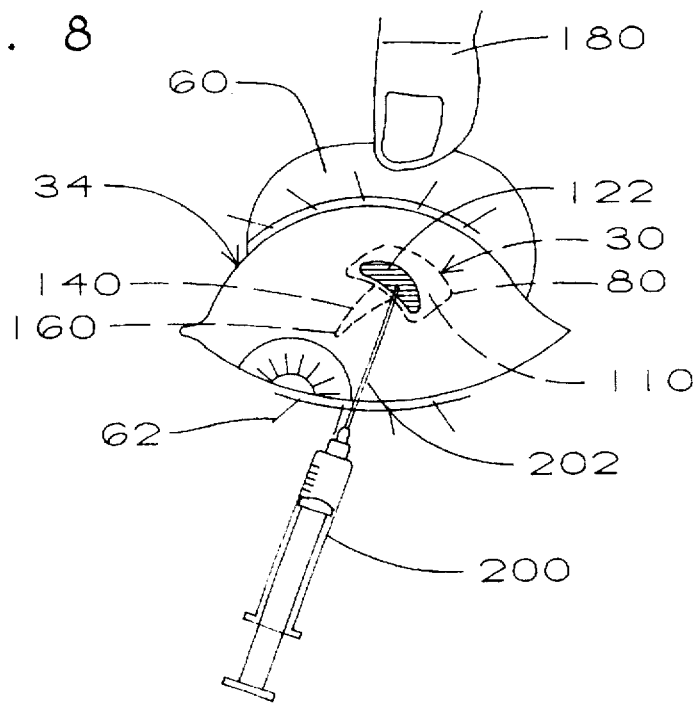
FIG. 9 is similar to FIG. 8, still enlarged but on a smaller scale, and demonstrating how the injection port of the subject device can be readily identified through overlying tissue.

This movement of medicine 194 (FIG. 2) from the storage reservoir 110 into the vitreous cavity 66 will normally continue, or be forced to flow by the patient's pumping of the tube 140, for an extended period of time whereupon it may be necessary to replenish the original supply of the medicine. Also, because of the discovery of a new and better drug or the need for a different drug or other medicine, it may be desirable to change the medication. In any case, the patient returns to the physician's office for the following simple procedure. The eyelid 60 is lifted (FIGS. 8 and 9) and the patient looks down to expose the region of the implanted delivery device 30. The scleral patch 190, the conjunctiva and Tenon's capsule 44 and a fibrous capsule (not specifically shown in the drawings but believed to be well understood), which grows over the device under the conjunctiva obscures the device 30, except for the injection port 122, as illustrated in FIG. 9. The port is visible through the tissue because it is identified with a color which can be seen through the tissue.

While digitally compressing the tube 140 (FIGS. 8 and 9) to block the passageway 144, as previously described, the injection port 122 is penetrated with the syringe needle 202 and a new supply of medicine 194 is injected into the reservoir 110. As previously indicated, venting of the implant reservoir 110 may be required for injection of larger volumes of medicine. Pressure on the tube is released and the needle is withdrawn, the port sealing after the withdrawal. The intravitreal delivery device 30 is then capable of repeating its delivery of medicine to the vitreous cavity 66 over an extended period of time, as previously described. Of prime significance, a repeat surgery to re-introduce a new implant, or another invasive procedure to inject a supply of medicine, is avoided.

A significant relationship between the location of the suturing tabs 98, 102, and 172 and the injection port 122 is to be noted. With reference to FIG. 1, it will be seen that all the sutures 184 are located anteriorly of the port. Thus, when the injection needle 202 (FIG. 9) presses against the port to thrust the needle through the port, the sutured tabs resist posterior movement of the implant device, as 30, and maintain it in its implanted position.

Intravitreal Delivery Device-Second Embodiment

The second embodiment 30a (FIGS. 10–12) of the present invention is the same as the first embodiment except that a valve 250 is incorporated in the elbow 160 to enhance the pumping action previously described. The valve shown and described is a ball-check valve, but other valves having a similar function can be employed. The valve shown, however, includes a valve body 252 fitted in the connector sleeve 162. The valve body provides an outer chamber 254 having an annular inlet 256 opening into the passageway 144 of the tube 140, an annular outlet 258 opening toward the intravitreal extension 164, an annular valve seat 260 between the inlet and outlet, and a dosage chamber 264 between the valve seat and the outlet. The valve also includes a resiliently expandable, conical mouthpiece 268 of a suitable elastomeric material whose apex is normally closed in its relaxed condition but which opens when fluid pressure inside the valve body, in the direction of the apex, forces it open. Still further, the valve includes a resilient ball 270 in the outer chamber and a spring 272 between the ball and the valve seat.

Figure 10:
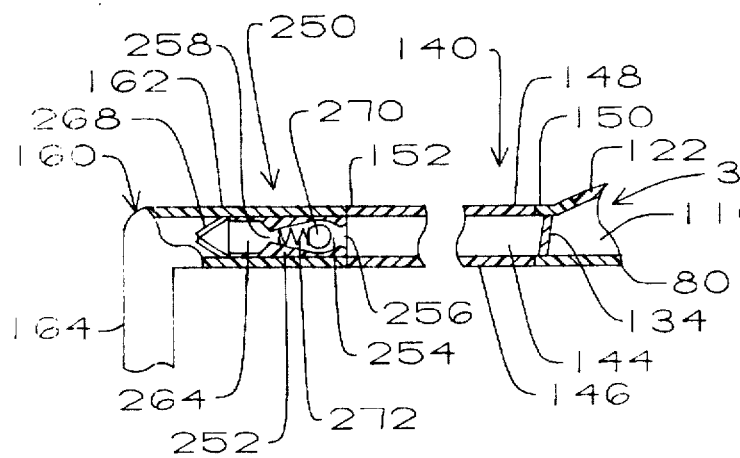
FIGS. 10 and 11 are both cutaway, sectional views of a portion of the intravitreal medicine delivery device of the present invention illustrating a valve in the elbow, with FIG. 11 showing the valve in a different position from FIG. 10.
Figure 11:
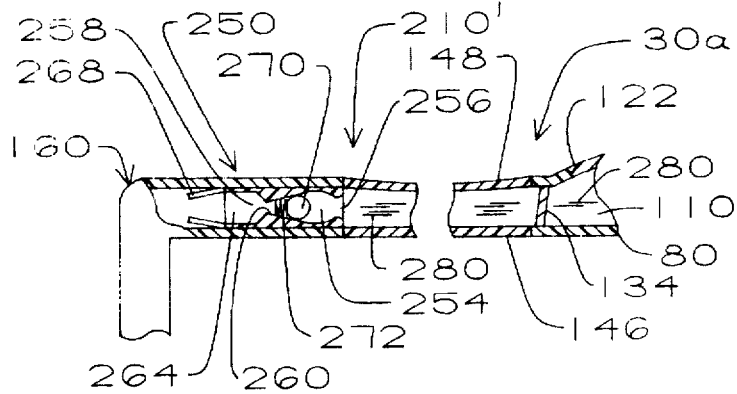
Figure 12A:
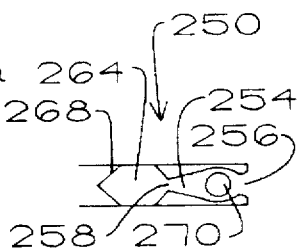
FIGS. 12a, 12b, 12c, 12d and 12e are schematic views showing the sequence of positions of the valve of FIGS. 10 and 11.

In operation of the intravitreal delivery device 30a when it incorporates the valve 250 (FIGS. 10–12), the storage reservoir 110 is filled with fluid-borne medicine, as represented by the numeral 280, either during initial manufacture or by subsequent injection through the injection port 122. With reference to the flow diagrams of FIGS. 12a–12e, the condition of the valve in its resting state is shown in FIG. 12a wherein the ball 270 floats in the outer chamber 254 being held away from the seat 260 by the spring 272 (FIG. 10). Because of the pressure gradients previously described in regard to the first embodiment, fluid-borne medicine from the reservoir fills not only the passageway 144 but also the outer chamber 254 (FIG. 11) and the dosage chamber 264. Under these conditions, there is insufficient pressure to open the mouthpiece 268.

Figure 12B:
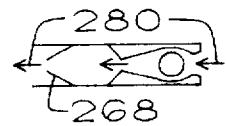
Figure 12C:
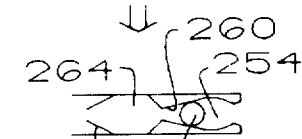
Figure 12D:
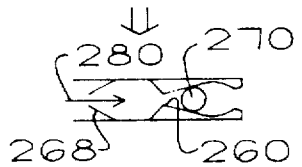

When a dose of medicine 280 is to be delivered to the vitreous cavity 66, the patient or attendant presses against the patient's eyelid 60 thereby pressing against the tube wall 148 (FIG. 11) compressing the tube 140 and constricting the passageway 144 and exerting a fluid pressure toward the vitreous cavity 66 (FIG. 12b). This pressure increase is sufficient to force the ball 270 against the spring 272 until the ball seals (FIG. 12c) against the seat 260 thereby temporarily blocking fluid flow through the valve. Such pumping action thus causes a limited quantity of fluid, essentially the amount in the dosage chamber 264, that is, the predetermined dose or aliquot, to flow into the vitreous cavity 66. Thus, the valve 250 and the tube 140, working in cooperative relationship with the reservoir 110 and the elbow 160, constitute a pump 210'.

Figure 12E:
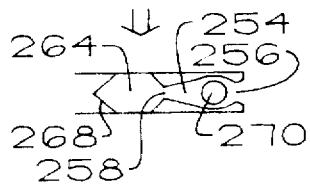

When pressure on the eyelid 60 and thus the tube wall 148 is relieved (FIGS. 12d and 12e), a reverse pressure develops because of the lowering of pressure in the passageway 144, whereby the valve ball 270 unseats, and the mouthpiece 268 collapses to its closed position. Fluid pressure in the device then returns to an equilibrium state and the valve returns to its resting state, as shown in FIG. 12e.

Intravitreal Delivery Device-Third Embodiment

Figure 13:
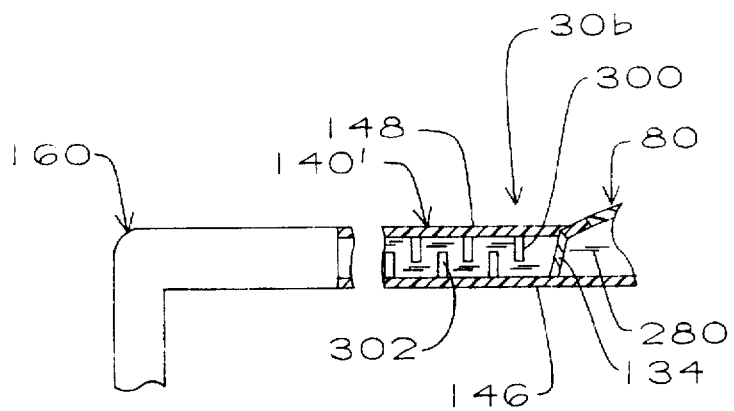
FIG. 13 is a cutaway sectional view of a portion of the subject delivery device and showing an optional feature in the tube of the device.

The third embodiment 30b of the present invention is the same as the first embodiment 30 except as follows. In FIG. 13, there is illustrated a tube 140' connected to the housing 80 and the elbow 160. A series of upper and lower baffles 300 and 302 are respectively attached to the top and base walls 148 and 146 of the tube and project into the passageway 144 in interdigitated, spaced relationship. Since the tube is oval, the baffles are semi-oval or semi-elliptical, but if a tube has a different cross-section, the shape of the baffles would be changed to conform. For example, if the tube is circular, the baffles would be semi-circular. The purpose of these baffles is to facilitate closure of the passageway when the walls of the tube are compressed during filling the storage reservoir 110, while allowing flow through the passageway at all other times when the tube is in normally fully expanded or open condition.

Intravitreal Delivery Device-Fourth Embodiment

The fourth embodiment of the delivery device is identified by the numeral 30c and relates to a different housing construction but is otherwise the same as the first embodiment 30. In FIG. 14, there is shown a housing 80' enclosing a reservoir 110' which is in communication with a tube, such as 140 or 141', which is only partially shown in FIGS. 14–16 since this embodiment does not involve a modification of the tube. The modified housing 80', however, has a base wall 84' like the base wall 84 (FIG. 6) and injection port 122' like the injection port 122 (FIGS. 3–6), but a top wall 86' different from the top wall 86 (FIG. 4). The top wall 86' (FIG. 14) has a main portion 124' including a peripheral section 326 and a medial section or roof 328 located posteriorly of the injection port 122'.

As best shown in FIGS. 14 and 15, the peripheral section 326 (excluding the injection port 122') is made of relatively rigid, impenetrable material, such as described for the base wall 84 and the main portion 124 of the first embodiment 30. The injection port 122' is constructed of the same penetrable, resealable material as the port 122. The medial section 328, however, is made of a softer, flexible and resilient material, such as silicone rubber, to allow the medial section or roof to be compressed and thereafter expand to its relaxed state. In addition, this medial section may be semi-permeable to preclude a vacuum from developing in the reservoir when the tube 140 or 140' is compressed while minimizing any appreciable loss of fluid-borne medicine.

Alternatively, the medial section 328 may be made of an elastomeric material which is distended by the injection of a large volume of medicine into the reservoir 110' via the injection port 122'. The distention of the medial section increases the pressure in the reservoir and forces drug-containing fluid into the tube 140 or 140' where egress into the vitreous is controlled by passage through a filter or capillary tube 134'. Still further, the entire housing 80' may be made of elastomeric material to provide such pressure by distention of the housing.

Intravitreal Delivery Device-Fifth Embodiment

The fifth embodiment (FIG. 17) involves a differently shaped housing 80", to which reference was previously made. Instead of the housings 80 or 80', each of which has a generally rectangular periphery, the housing of this embodiment has a generally trapezoidal outline in plan view. Such a trapezoidal shape may be preferred to facilitate implantation. The trapezoidal housing has an injection port 122", anterior tabs 98" with suture eyelets 100", and lateral tabs 340 with suture eyelets 342. Again, by way of example only, the preferred dimensions of the trapezoidal housing are similar to the rectangular housing except that the posterior edge is about 1.5 cm and the anterior edge is about 0.75 cm.

Intravitreal Delivery Device-Additional Feature

An additional feature which may be incorporated in the previously described embodiments of the present invention has two species as shown in FIGS. 18 and 19. In FIG. 18, there is illustrated a tubular elbow 160a having an intravitreal extension 164' in which is provided a plurality of holes or slits 350. A semi-permeable wick, insert, or filter 352 of very flaccid material, such as a silicone sponge, is positioned in the passageway of the extension.

In FIG. 19, a semi-permeable membrane or filter 360 in the shape of a relatively rigidly-formed cup is attached to the open tip 166' of a tubular elbow 160b and projects therefrom.

When either species shown in FIGS. 18 and 19 is incorporated in the intravitreal delivery device 30, 30a or 30c of the present invention, medicine passes from the reservoir 110 through the passageways 144 and 168 and through the wick 352, or the membrane 360, from which it diffuses into the vitreous cavity 66. The wick or membrane is optionally used to obviate the possibility of occlusion of the drug passage into the vitreous cavity by particulate matter from the reservoir.

From the foregoing description of the intravitreal medicine delivery device 30, 30a, 30c and method of the present invention, it will be understood how the device and method result in numerous advantages and provide solutions to various problems experienced by prior art devices and methods. The subject invention enables a wide variety of drugs and other pharmacological agents and medicines to be introduced into the vitreous cavity over the lifetime of the patient with only a single initial surgery and with minimum intraocular invasion to implant the device.

Thereafter, to resupply the device 30 with more medicine or to change the medicine, only a simple injection into reservoir 110 through the specially identifiable injection port 122, 122', or 122" of the device is necessary. No invasive surgery or procedure is needed.

As contrasted with biodegradable polymer pellets directly implanted into the eyeball and which do not lend themselves to many potential pharmacological agents, the subject device 30 is not so limited and can utilize the broad range of medicinal agents now available or becoming available. Moreover, the device 30 and method allow the dosage delivered to the vitreous cavity 66 to be controlled and furthermore, allows the patient to control the timing of the deliveries. Additional features incorporated into the device filter the medicine before it enters the vitreous cavity. Also, the device is designed to facilitate its implantation so that it fits closely and relatively comfortably against the eyeball and so that damage or interference with other parts of the eye are avoided.

Although preferred embodiments have been shown and described, various modifications and substitutions may be made thereto without departing from the spirit and scope of the invention. Accordingly, it is to be understood that the present invention has been described by way of illustration and not limitation.

What is claimed is:

1. An intravitreal medicine delivery device for delivering medicine to the vitreal cavity of an eye having an eyeball covered by conjunctiva, comprising reservoir means for holding a supply of medicine, means for enabling passage of medicine out of the reservoir means, and means for attaching both the reservoir means and the enabling means under the conjunctiva of an eye so that the entire device is under the conjunctiva, said enabling means being adapted to enable passage of medicine into the vitreal cavity of the eye.

2. The device of claim 1 wherein the reservoir means includes means for filling the reservoir means while the reservoir means and the enabling means both remain under the conjunctiva.

3. The device of claim 2 wherein the reservoir filling means is capable of being visible through the conjunctiva when implanted.

4. The device of claim 1 wherein the reservoir means includes means for pumping medicine into the vitreal cavity.

5. The device of claim 4 wherein the pumping means includes valve means which allows fluid-borne medicine to flow from the reservoir means into the vitreal cavity but restricts fluid flow from the vitreal cavity into the reservoir means, and wherein the pumping means also includes a compressible and expandable portion of the enabling means which upon expansion draws fluid-borne medicine from the reservoir means and upon compression, forces fluid-borne medicine into the vitreal cavity.

6. The device of claim 1 wherein the enabling means includes a fluid passageway having a proximate end in communication with the reservoir means and a distal end adapted for communication with the vitreal cavity, said passageway being resiliently compressible to constrict and expand the passageway thereby to draw fluid-borne medicine from the reservoir means into the passageway through said proximate end and to pump fluid-borne medicine from the passageway out of the distal end into the vitreal cavity, said enabling means further including means for allowing fluid flow out of the reservoir means but restricting flow into the reservoir means.

7. The device of claim 1 wherein the reservoir means includes an anteriorly facing injection port penetrable by an injection needle when the needle is forced into the port but fluid-impervious when the needle is withdrawn, and wherein the attaching means includes means for attaching the reservoir means adjacent to the vitreal cavity at a location anteriorly of the injection port so that said attaching means resists movement of the reservoir means when an injection needle applies force against the port.

8. A device for delivering medicine into the vitreous cavity of an eye including an eyelid and an eyeball, said eye also having conjunctiva and Tenon's capsule covering the eyeball, comprising a housing having a reservoir for holding a supply of medicine, a tube having one end connected to the housing in communication with the reservoir and an opposite end, and means for attaching the housing to an eyeball so that the housing and both ends of the tube are under the conjunctiva and Tenon's capsule whereby the housing and the tube are covered by the conjunctiva and Tenon's capsule, said opposite end of the tube being adapted to project through the eyeball into the vitreous cavity, the housing having wall portions surrounding the reservoir, one of said wall portions including a reservoir refilling means which faces anteriorly of the eye when the housing is attached to the eyeball and which is then accessible to a refilling instrument, said refilling means allowing a refilling instrument to introduce medicine through the conjunctiva and Tenon's capsule into the reservoir but preventing medicine from escaping from the reservoir.

9. The delivery device of claim 8 wherein said refilling means has a predetermined marking which after the housing is attached is capable of being visible through the conjunctiva and Tenon's capsule exteriorly of the eye when the eyelid is lifted, said marking distinguishing said refilling means to facilitate its location.

10. The delivery device of claim 9 wherein said marking is a color.

11. The delivery device of claim 8 wherein the reservoir refilling means is a port area of a material which is normally fluid-impervious but which can be penetrated by a sharp refilling instrument, and wherein wall portions of the housing are impenetrable to the injection instrument except for said port area.

12. The delivery device of claim 8 wherein said reservoir has an inside and an outside, wherein at least part of the wall portions of the housing is semi-permeable to minimize the pressure differential between the inside and the outside of said reservoir.

13. The device of claim 8 wherein the wall portions include a base wall and a top wall joined to the base wall, said base wall having a curvature generally complementary to the curvature of an eyeball, said top wall including a needle-penetrable and resealable port constituting said refilling means, and a remainder portion, the base wall and the remainder portion of the top wall being impenetrable by an injecting needle.

14. The device of claim 8 wherein the wall portions include a relatively hard base wall impenetrable by a sharp instrument and shaped to fit against an eyeball and a top wall in closely spaced relationship to the base wall to define a minimal height dimension of said reservoir, said reservoir having lateral dimensions relatively much greater than said height dimension, said lateral dimensions extending spherically of the eyeball when the base wall is positioned on the eyeball, and wherein the top wall includes an injection area constituting the refilling means and a medial roof area, said injection area being penetrable by a sharp injection instrument but being reseatable when the instrument is withdrawn, said medial roof area being soft and flexible enough to allow its compressibility toward and away from the base wall, and said top wall being otherwise relatively hard and impenetrable by a sharp injection instrument.

15. An intravitreal medicine delivery device for delivering medicine to the vitreal cavity of an eyeball covered by conjunctiva and within an eye socket, comprising reservoir means for holding a supply of medicine, means for attaching the reservoir means within an eye socket exteriorly of and closely adjacent to the eyeball, means for enabling passage of medicine from the reservoir means into said vitreal cavity, said reservoir means including a relatively low-profile housing having an eyeball-shaped, spherical curvature adapted to fit closely against the eyeball under the conjunctiva and Tenon's capsule, said housing including a reservoir having a minimal height dimension measured radially of said curvature and lateral dimensions measured spherically of the housing and being substantially greater than the height dimension, said enabling means including a tube projecting from the housing and having an angular extension for projecting into the vitreal cavity.

16. The device of claim 15 wherein the housing has a medicine injecting port facing outwardly from the housing in the same direction that the tube projects from the housing.

17. An intravitreal medicine delivery device for delivering medicine to the vitreal cavity within an eyeball in the socket of an eye in a living body, comprising a housing having a reservoir capable of containing medicine; means for attaching the housing within the socket of an eye adjacent to the vitreal cavity of the eyeball; means for conducting medicine in a fluid medium from the reservoir into the vitreal cavity; and valve means in the conducting means, actuatable exteriorly of the body in which the eye is located, and having a dosage chamber in communication with said reservoir adapted to communicate with the vitreal cavity through the conducting means, said valve means being actuatable to enable a predetermined dosage of medicine to be collected in the dosage chamber and to be forced therefrom through said conducting means into the vitreal cavity.

18. The device of claim 17 wherein said valve means includes a valve body having an inlet port communicating with the reservoir, an annular outlet port defining a valve seat and spaced from the inlet port, a conical seal having a base connected to the outlet port and a resiliently distendible apical mouth projecting away from the outlet port, said mouth being normally closed when relaxed but opening under internal fluid pressure, said dosage chamber being defined by the space between the closed mouth and the outlet port, a ball between the inlet and outlet ports and adapted to float in fluid in the valve, and a spring between the valve seat and the ball which normally prevents the ball from contacting the valve seat but yields under fluid pressure to cause the ball to contact the valve seat after a predetermined dose of fluid passes through the outlet port into the dosage chamber.

19. An intravitreal medicine delivery device for delivering medicine to the vitreal cavity of an eyeball covered by conjunctiva and within an eye socket, comprising reservoir means for holding a supply of medicine, means for attaching the reservoir means within an eye socket exteriorly of and closely adjacent to the eyeball, means for enabling passage of medicine from the reservoir means into said vitreal cavity, the medicine in the reservoir being incorporated in particulate matter from which it diffuses, said enabling means including means for controlling the diffusion of medicine from the reservoir means into the vitreal cavity while restricting passage of said particulate matter into said cavity.

20. The device of claim 19 wherein the enabling means has a proximate end connected to the reservoir means, and wherein the diffusion controlling means is a semi-permeable member positioned at the proximate end of the enabling means.

21. The device of claim 19 wherein the enabling means has a distal end adapted to project into the vitreal cavity, and wherein the diffusion controlling means is a semi-permeable member positioned at the distal end of the enabling means.

22. The device of claim 21 wherein said distal end is a perforate tubular extension, and wherein said semi-permeable member is positioned in the extension.

23. An intravitreal medicine delivery device for delivering medicine to the vitreal cavity of an eyeball covered by conjunctiva and within an eye socket, comprising reservoir means for holding a supply of medicine, means for attaching the reservoir means within an eye socket exteriorly of and closely adjacent to the eyeball, means for enabling passage of medicine from the reservoir means into said vitreal cavity, and means for restricting passage of materials from the vitreal cavity into the reservoir means and for preventing non-medicinal materials from moving into the vitreous cavity.

24. A device for delivering medication to the vitreous cavity of an eyeball comprising a housing having a plastic wall surrounding a reservoir for holding medication, said wall having a base of a first plastic material impenetrable to an injection instrument and adapted to fit complementarily against an eyeball, a top joined to the base having posterior and anterior portions and including an injection area in the anterior portion, said top being also of said first plastic material except for the injection area, said injection area being of a second plastic material which is penetrable by an injection instrument but which reseats after the instrument is withdrawn, and means connected to the housing in communication with the reservoir and projecting anteriorly away from the housing for insertion into the vitreous cavity of the eyeball for allowing movement of medicine from the reservoir into the vitreous cavity.

25. An intravitreal medicine delivery device for delivering medicine to the vitreal cavity of an eyeball covered by conjunctiva and within an eye socket, comprising reservoir means for holding a supply of medicine, means for attaching the reservoir means within an eye socket exteriorly of and closely adjacent to the eyeball, means for enabling passage of medicine from the reservoir means into said vitreal cavity, the medicine in the reservoir being incorporated in particulate matter, and means for preventing passage of particulate matter from the reservoir means into the vitreal cavity.

26. An intravitreal medicine delivery device for delivering medicine to the vitreal cavity in the eyeball of an eye, comprising a relatively rigid, pre-formed plastic housing substantially all of which is of fluid-impervious material for holding a supply of medicine, said housing having a peripheral edge including anterior and posterior portions joined by opposed lateral portions, an outwardly convex top wall, and an outwardly concave bottom wall adapted to fit against an eyeball, said opposed portions of the peripheral edge being spaced by a lateral distance substantially greater than a height dimension between said top and bottom walls whereby said housing has a flat profile so as to hug an eyeball against which the bottom wall is placed, an elongated tube of fluid-impervious material and of oval cross-section and being connected to the housing in fluid communication therewith, said tube having a major axis and a minor axis, and a fluid-conducting elbow connected to the tube and having a terminal end projecting angularly from the tube for extension into the vitreal cavity of said eyeball, said tube projecting anteriorly of the housing and with its major axis converging anteriorly between the housing and the elbow.

27. An intravitreal medicine delivery device for delivering medicine to the vitreal cavity of an eyeball covered by conjunctiva and within an eye socket, comprising reservoir means for holding a supply of medicine, means for enabling passage of medicine from the reservoir means into said vitreal cavity, means for attaching the reservoir means and the enabling means under the conjunctiva within an eye socket exteriorly of and closely adjacent to the eyeball so that the entire device is under the conjunctiva, the reservoir means having wall means for holding a supply of medicine, the enabling means having wall means providing a passageway through which medicine can pass from the reservoir means to the vitreal cavity, and at least one of said wall means including a resiliently movable portion for applying pressure to move medicine from the reservoir means into the cavity.

28. An intravitreal medicine delivery device for delivering medicine to the vitreal cavity of an eyeball covered by conjunctiva and within an eye socket, comprising reservoir means for holding a supply of medicine, means for attaching the reservoir means within an eye socket exteriorly of and closely adjacent to the eyeball, means for enabling passage of medicine from the reservoir means into said vitreal cavity, the enabling means being a resiliently compressible tube having upper and lower walls defining a passageway which contracts and expands in response to compression and release of the tube and including spaced upper and lower baffles mounted on the upper and lower walls respectively and projecting into the passageway toward the opposite wall to close the passageway when the passageway is contracted but to allow fluid flow when the passageway is expanded.

* * * * *